United States Patent [19]

Seo

[11] Patent Number: 4,501,279
[45] Date of Patent: Feb. 26, 1985

[54] ULTRASONIC BLOOD FLOW SENSING APPARATUS

[75] Inventor: Yasutsugu Seo, Ootawara, Japan

[73] Assignee: Tokyo Shibaura Denki Kabushiki Kaisha, Kawasaki, Japan

[21] Appl. No.: 418,001

[22] Filed: Sep. 14, 1982

[30] Foreign Application Priority Data

Sep. 18, 1981 [JP] Japan .............................. 56-146311

[51] Int. Cl.³ ............................................ A61B 10/00
[52] U.S. Cl. ................................................... 128/663
[58] Field of Search ..................... 128/663; 73/861.25; 128/661

[56] References Cited

U.S. PATENT DOCUMENTS

| 4,217,909 | 8/1980 | Papadofrangakis | 128/663 |
| 4,271,842 | 6/1981 | Specht | 128/661 |
| 4,370,985 | 2/1983 | Takeichi et al. | 128/663 |
| 4,373,533 | 2/1983 | Iinuma | 128/663 |
| 4,416,286 | 11/1983 | Iinuma | 128/663 |

OTHER PUBLICATIONS

Brandestini, M., "Topoflow-a Digital Full Range Doppler Velocity meter", IEEE Trans. on Sonics & Uts., vol. SU-25, No. 5, Sep. 1978.
Baker, D. W., "Pulsed Doppler Blood Flow Sensing", IEEE Trans. on Sonics and Uts. SU-17, 170Z185, 1970.
Matsuo, H. et al., "Development of Ultrasound System Combining an Electronic Beam Sector Scanner and a Pulsed Doppler Flow Meter and its Clinical Application", papers at the 34th Japan Ultrasonic Medical Society, p. 7, 1978.

Iinuma, K., "Ultrasound Imaging Techniques" bulletin in Television Society, vol. 35, No. 1, p. 2, 1981.

Primary Examiner—Kyle L. Howell
Assistant Examiner—Francis J. Jaworski
Attorney, Agent, or Firm—Cushman, Darby & Cushman

[57] ABSTRACT

An ultrasonic Doppler blood flow sensing apparatus comprises a probe for sending an ultrasonic wave into a living body and receiving echoes, an ultrasonic diagnosing device for processing the echoes received to provide a tomogram signal, an ultrasonic Doppler blood flow meter for processing the echoes received to provide blood flow data, an electrocardiographic circuit, a gate for producing a sampling signal in response to an electrocardiographic signal from the electrocardiograph circuit, a random access memory for sampling and storing blood flow data sensed by the blood flow meter in response to the sampling signal from the gate, detectors for detecting a radius r of a blood vessel and a cosine of $\theta$, where $\theta$ is an angle of direction of an ultrasonic beam with respect to a direction of blood flow at a part of the living body to be measured on the basis of the tomogram data derived from the diagnosing device, an arithmetic logic unit for calculating an average blood flow during a most recent one minute or for one or several most recent cardiac cycles on the basis of the sampled blood flow data stored in the RAM, the detected $\cos \theta$ from the cosine detector and the radius r of the blood vessel from the r detector, and a monitor for displaying a tomogram defined by the tomogram data from the diagnosing device and an average blood flow from the arithmetic logic unit.

7 Claims, 26 Drawing Figures

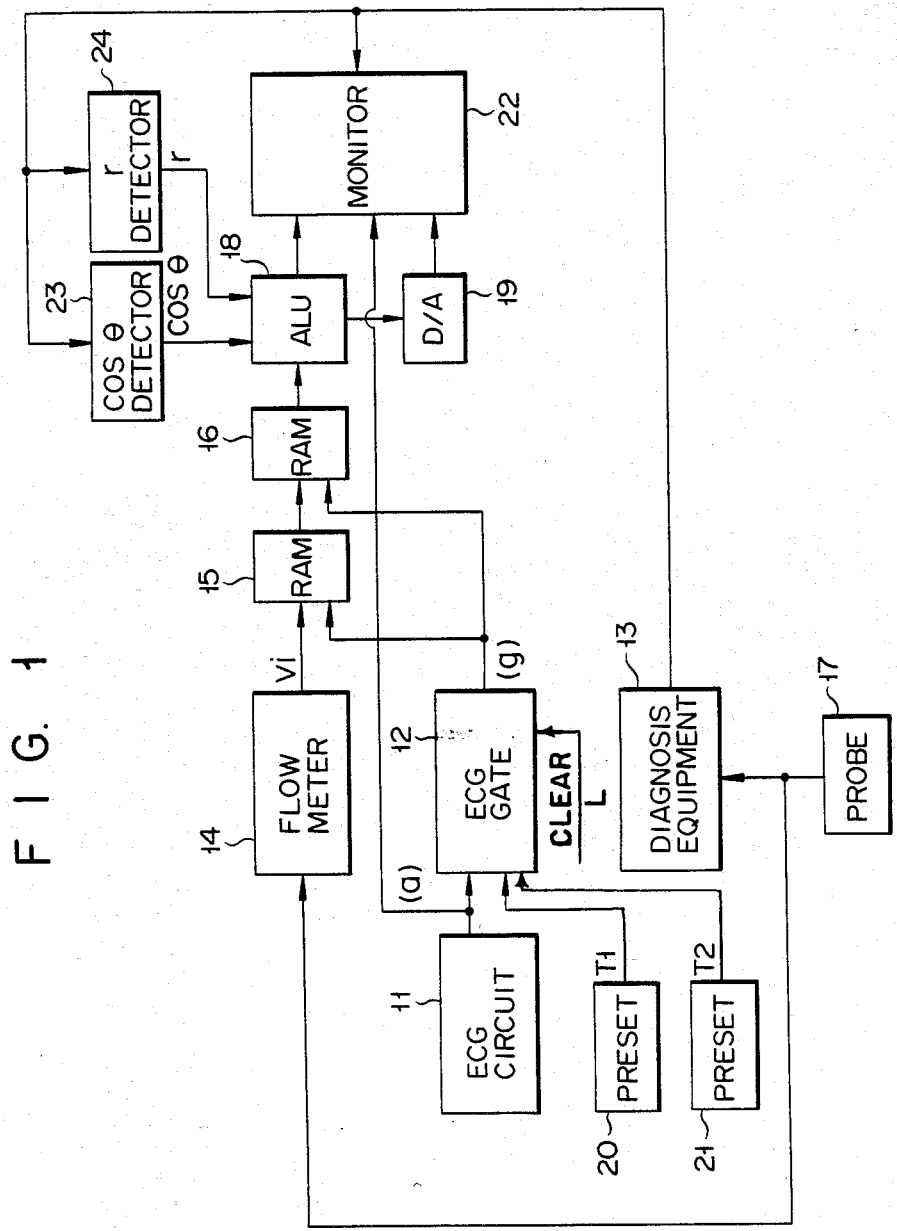
F I G. 1

F I G. 6
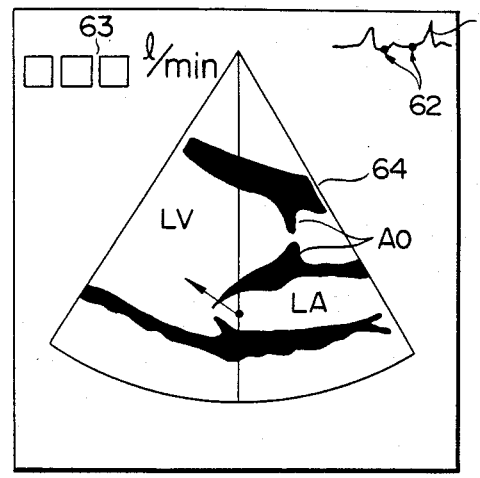
F I G. 7
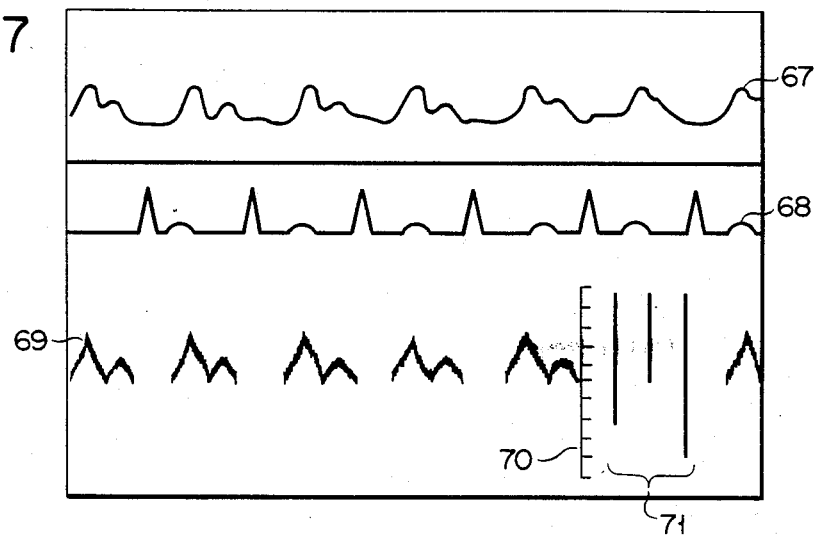
F I G. 8
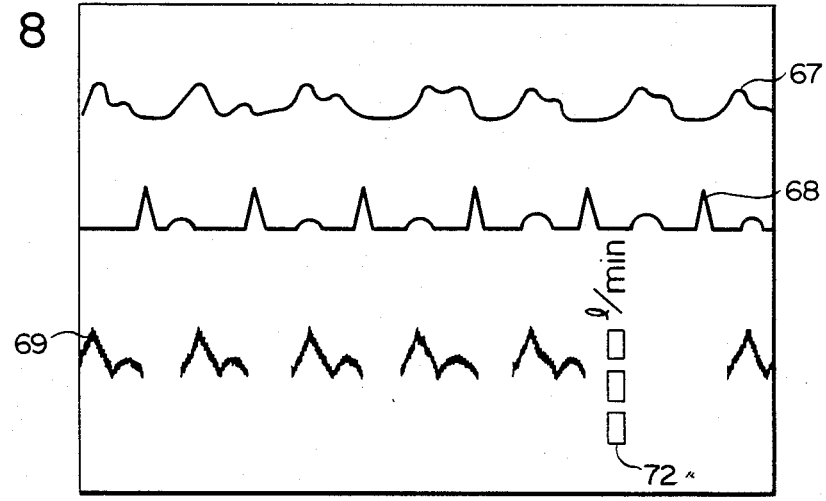

ULTRASONIC BLOOD FLOW SENSING APPARATUS

BACKGROUND OF THE INVENTION

The present invention relates to an ultrasonic blood flow sensing apparatus incorporating an ultrasonic diagnosis device using ultrasonic tomography and a Doppler blood flow meter using an ultrasonic Doppler method.

The Doppler flow meter has not been used frequently in diagnosis because it cannot accurately isolate on a specific part of a living body at which a blood flow measurement is desired. Recently, a proposal to overcome this problem, as described in papers at the 34th *Japan Ultrasonic Medical Society* page 7, published 1978, combines a blood flow meter and an ultrasonic diagnostic apparatus using ultrasonic tomography, enabling an operator to accurately specify a location of an affected part of a living body for blood flow measurement. The approach will be described briefly. In this blood flow sensing apparatus, an ultrasonic wave is transmitted, by a transducer probe, into a subject under blood flow measurement. Echoes returned from the inside of the subject are received by the probe. Of the echoes received, only the echoes reflected from a specific or affected part of the subject, in which the blood flow is to be measured, are sampled, and the sampled echoes are passed through a band pass filter where the Doppler frequency shift of the echoes is obtained. The Doppler frequency shift thus obtained is treated as blood flow data because it has a proportional relationship to a velocity of the blood flow. A signal representing the Doppler frequency shift is subjected to frequency analysis by a frequency analyzer. The analyzed signal is displayed on a screen of a display unit in which the abscissa coordinate represents time and the ordinate represents a velocity of blood flow proportional to the Doppler frequency shift. Incidentally, the frequency analyzer used is, for example, a fast Fourier transformer (FFT) frequency analyzer capable of processing 128 data items within 2 msec., as described in *bulletin in Television Society* Vol. 35, No. 1, page 2, 1981.

The prior blood flow sensing apparatus measures and displays an average velocity of blood flow (referred to as an instantaneous average blood flow) averaged in a time range from the start of the blood flow measurement to a proper time point. For securing an accurate diagnosis, however, an average blood flow for one minute, or for one to several cardiac cycles prior to the present time point is required. The former and latter blood flows will be referred to as an average per-minute blood flow and an average per-cardiac cycle blood flow, respectively.

SUMMARY OF THE INVENTION

Accordingly, an object of the present invention is to provide an ultrasonic blood flow sensing apparatus incorporating a combination of a Doppler blood flow meter and an ultrasonic diagnosis apparatus, which may display an average per-minute blood flow or an average per-cardiac cycle blood flow.

According to the invention, there is provided an ultrasonic Doppler blood flow sensing apparatus comprising: transducing means for sending an ultrasonic wave into a subject and receiving echoes from the same; ultrasonic diagnosing means for processing the echoes received to provide a tomogram signal; ultrasonic Doppler blood flow meter means for processing the echoes received to provide blood flow data; means for sensing electrocardiographic data of the object; gating means for producing a sampling signal in response to an electrocardiographic signal from the electrocardiographic circuit means; means for sampling and storing blood flow data sensed by the blood flow meter means in response to the sampling signal from the gating means; means for calipering a radius r of a blood vessel on the basis of tomogram-derived data from the diagnosing means; angle sensing means for sensing a cosine of $\theta$ ($\cos \theta$) where $\theta$ is an angle of direction of an ultrasonic beam with respect to a direction of a blood flow at a part of the object to be measured on the basis of the tomogram data derived from the diagnosing means; arithmetic logic means for calculating an average blood flow during a specific latest period of time on the basis of the sampled blood flow data, the detected $\cos \theta$ and the radius r of the blood vessel; and display means for displaying a tomogram defined by the tomogram data from the diagnosing means and an average blood flow from the arithmetic logic means.

BRIEF DESCRIPTION OF THE DRAWINGS

FIG. 1 is a block diagram of an embodiment of an ultrasonic blood flow sensing apparatus according to the present invention;

FIGS. 6, 7 and 8 schematically illustrate some examples of displays on a screen of a monitor used in the blood flow sensing apparatus of FIG. 1.

DETAILED DESCRIPTION OF THE PREFERRED EMBODIMENTS

Figure 2:
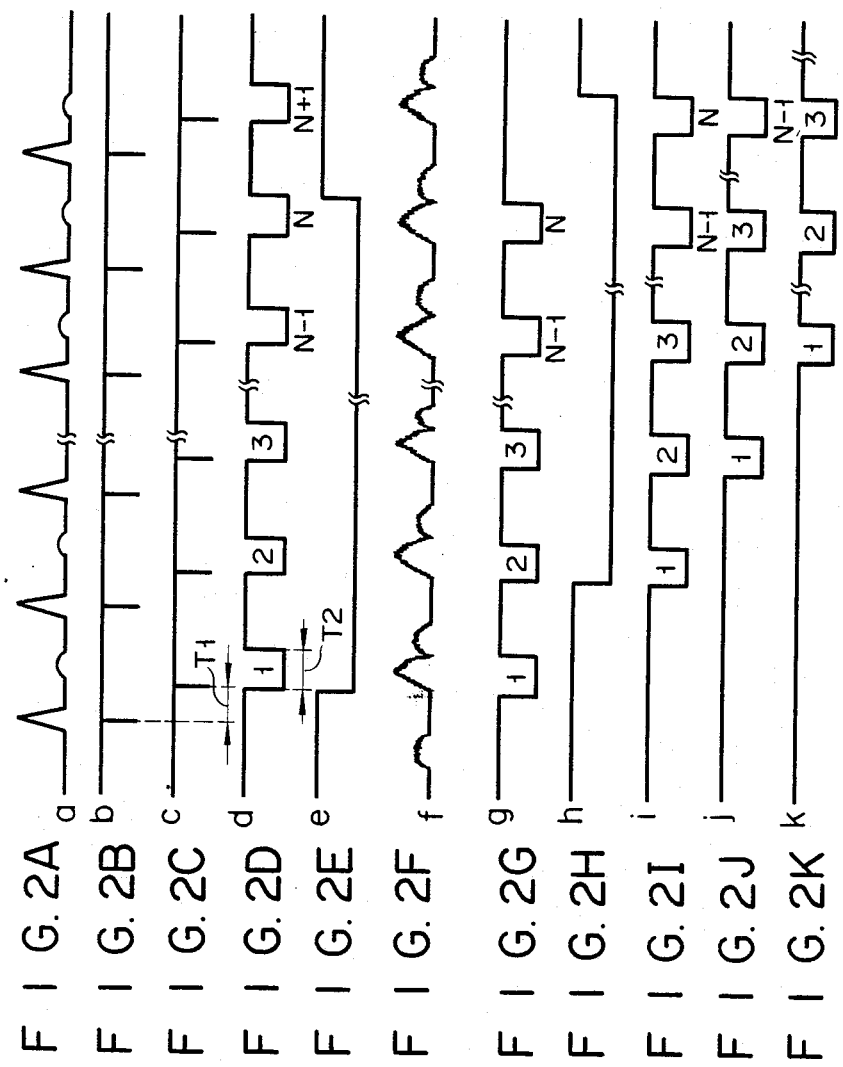
FIGS. 2A to 2K show a set of waveforms illustrating a sequential operation of the blood flow sensing apparatus of FIG. 1.

Referring to FIG. 1, there is shown a scheme of an ultrasonic blood flow sensing apparatus according to the present invention. In the figure, an electrocardiograph (ECG) circuit 11 provides a cardiographic signal (FIG. 2A) in an object. The ECG circuit 11 is connected at the output to a monitor 22 as a display unit for visualizing the cardiographic signal. An ECG gate 12 is connected to the output of the ECG circuit 11 and at the first and second control terminals (FIG. 4) to the outputs of first and second preset circuits 20 and 21. The gate 12 responds to the signal (FIG. 2A) from the ECG circuit 11 and preset signals from the first and second present circuits 20 and 21 to internal signals as shown in FIGS. 2B to 2E and to produce an output signal shown in FIG. 2G.

A probe 17 of the known sector electronic scanning type transmits an ultrasonic beam into the object (a living body) and receives echoes returned from the inside of the living body to convert into a corresponding electrical signal. The probe 17 is connected to the input of an ultrasonic diagnosis device 13 and the input of a Doppler blood flow meter 14. The flow meter 14 may be the one disclosed in bulletin in *Medical electron-* ics Society Vol. 17, No. 3, page 214, 1979, for example. The blood flow meter 14 is connected at the output to a random access memory (RAM) 15 for sampling and storing a blood flow signal from the blood flow meter 14. The RAM 15 is further connected to another RAM 16 for reading out the blood flow data from the former RAM 15. The RAMs 15 and 16 are connected at the control terminals to the output of the ECG gate 12. The output signal (FIG. 2G) from the ECG gate 12 is applied as a sampling signal for read and write operations to the RAMs 15 and 16. The output of the RAM 16 is connected to the first input terminal of an arithmetic logic unit (ALU) 18 for receiving the blood flow data from the RAM 16.

The ultrasonic diagnosis device 13 processes the echoes from the living body to provide data of a B scan tomogram.

Figure 3:
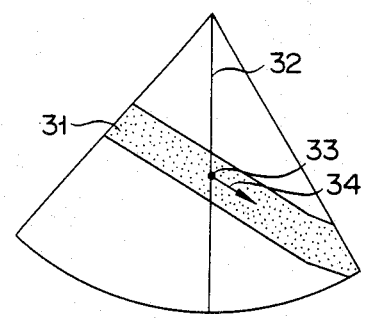
FIG. 3 schematically illustrates a cross section of a part under observation which is useful in explaining the operation of a cosine detector used in the blood flow sensing apparatus of FIG. 1.

The output of the ultrasonic diagnosis device 13 is connected to a monitor 12, a cosine detector 23 and a caliper circuit or an r detector 24. The cosine detector 23 calculates an angle $\theta$ of a direction of the ultrasonic beam with respect to a direction of the blood flow at a specific or effected part of the living body and its cosine, $\cos \theta$, on the basis of the tomogram data from the diagnosis device 13. The caliper circuit 24 detects a radius r of a blood vessel in the specific part of the living body, using the tomogram data from the diagnosis device 13. The cosine detector 23 and the caliper circuit 24 are connected to the second and third input terminals of ALU 18. The ALU 18 calculates an average latest blood flow, or an average per-minute or per-cardiac cycle blood flow, using the blood flow data from the readout RAM 16, the angle data of $\cos \theta$ from the cosine detector 23, and the r data from the caliper circuit 24. The output of the ALU 18 is connected directly and through a digital-to-analog (D/A) converter to the monitor 22. The monitor 22 visualizes the blood flow and its related data on the specific part of the living body on the basis of the output signals from the ALU 18, the D/A converter 19, the ECG gate 12 and the diagnosis device 13. For further details of the cosine detector 23, reference is made to Japanese Patent Application No. 15811/80 filed by the applicant of the present patent application. In FIG. 3, reference numeral 31 is a blood vessel, and 32 is a direction of the ultrasonic beam transmitted. A marker 34 with an arrow head is displayed on the monitor screen. In the cosine detector 23, the marker 34 is rotated about a point 33 centered at the specific part until it coincides with the direction of the ultrasonic beam 32. Then, the detector 23 obtains the angle $\theta$ of the blood flow with respect to the beam direction from the rotating angle data, and logically determines a cosine of $\theta$.

The operation of the ultrasonic blood flow sensing apparatus thus arranged will now be described.

The probe 17 is excited to send an ultrasonic beam into the living body, and receives the echoes from the living body to convert it into a corresponding electrical signal. The electrical echo signal is applied to the diagnosis device 13 and to the Doppler flow meter 14. The diagnosis device 13 processes the echo signals from the living body to provide data of a B scan tomogram. The tomogram data is then applied to the monitor 22 where it is visualized on a screen, and is also applied to the cosine detector 23 and the r detector 24. The cosine detector 23 obtains an angle $\theta$ of the blood flow direction at the specific part or location against the direction of the ultrasonic beam emitted from the probe 17, using the tomogram data received and then calculates a cosine of $\theta$ ($\cos \theta$). The $\cos \theta$ data is applied to the ALU 18. The r detector 24 calculates a radius r of a blood vessel at the specific location using the tomogram data. The r output signal is also applied to the ALU 18.

The Doppler flow meter 14 picks up only the echo signals returned from the specific location from among all the incoming echo signals in order to obtain a Doppler frequency shift and thus a blood flow.

The ECG circuit 11 detects an electrocardiographic signal as shown in FIG. 2A. The cardiographic signal is applied to the first input terminal of the ECG gate 12 and to the monitor 22 where it is visualized. The ECG gate 12 is further applied with a preset signal for setting a given delay time T1 derived from the first preset circuit 20 and another preset time for setting a given sampling period T2 derived from the second switch circuit 21. The ECG gate 12 internally, using these input signals, a trigger signal (FIG. 2B) in synchronism with the peak of an R wave of the cardiographic signal, a signal (FIG. 2C) is the trigger signal delayed a delay time T1, a sampling pulse signal (FIG. 2D) with a pulse width T2 necessary for obtaining an average current of blood flow Doppler shift (FIG. 2F), and a pulse signal (FIG. 2E) for setting a period sampled by the sampling pulse signal to a period of N cardiac cycles. It also outputs a read/write signal or a sampling signal (FIG. 2G) used as a write signal for the RAM 15 and a read signal for the RAM 16. The number N of cardiac cycles is a natural number and set to N=5, in order that any influence by an arrhythmia is avoided.

The sampling signal of FIG. 2G is applied at the control terminal of the RAM 15. The RAM 15 samples and stores the blood flow data from the blood flow meter 14 according to the sampling signal from the ECG gate 12. The blood flow data is written into the RAM 15 in the form of the data of 8 bits per 2.67 msec., for example. The blood flow data stored in the RAM 15 is read out into the RAM 16 according to the sampling signal (FIG. 2G) applied also to the RAM 16. The blood flow data read out from the RAM 16 is applied to the ALU 18.

Thus, the blood flow data from the RAM 16, the $\cos \theta$ data from the cosine detector 23, and the r data from the r detector 24 are applied to the ALU 18. Using these data, the ALU 18 calculates an average per-minute blood flow Q1 and/or and average per-cardiac cycle blood flow Q2 as selected by an operator. This calculation procedure follows. Instantaneous average blood flow velocity signals Vi produced many times every cardiac cycle, for example, every 2.67 msec., are added to one another over a period of N cardiac cycles and then the resultant sum is divided by the number of additions M, representing the number of detections of vi by blood flow meter 14 over cardiac cycles. As a result, an average blood flow velocity $\overline{v1}$ per second (cm/s) is obtained. If an operator has selected determination of the per-minute average blood flow, Q1, ALU 18 performs the following calculation:

$$Q1 = 60\overline{v1} \cdot \frac{\pi r^2}{2} \cdot \cos \theta \ (l/min) \qquad (1)$$

It should be noted that the per-minute average blood flow Q1 does not designate the blood flow during the whole period of the most recent one minute, but designates the blood flow during the sampling period T2. If an operator has selected determination of the average per-beat blood flow, Q2, ALU 18 performs the following calculation:

$$Q2 = \frac{\overset{M}{\underset{i=1}{(\Sigma vi)}} \cdot \Delta t}{N} \cdot \frac{\pi r^2}{2} \cdot \cos\theta \text{ (l/beat)} \quad (2)$$

It should be noted that the average per-cardiac cycle blood flow Q2 does not designate the blood flow during the whole period of the most recent one cardiac cycle, but designates the blood flow during the sample period T2. In the equation (2), $\Delta t$ designates an interval at which a signal representing a blood flow velocity at a proper time point, or an instantaneous blood flow signal, is applied to the ALU 18, and is 2.67 msec., for example. N designates the number of cardiac cycles during the sampling period. M designates the number of instantaneous flow velocity detections in M cardiac cycles. In this way, the ALU 18 performs the above operations to obtain the per-minute average blood flow Q1 and/or the average per-cardiac cycle blood flow Q2. The result of the operation is directly applied to the monitor 22 where it is displayed in a digital fashion. The operation result is also applied through the D/A converter 19 to the monitor 22 where it is displayed in an analog fashion.

For obtaining the average blood flow during N beats, the above-mentioned method measures the time of N beats. The result of the average blood flow, however, may be obtained in a shorter cycle, in a manner that the average blood flow data on the N beats is stored, the stored data is shifted every time the average per-cardiac cycle blood flow data is obtained, and the shifted average blood flow data is used for calculation of the average blood flow over a period from the present beat to the past N−1 cardiac cycle.

Figure 4:
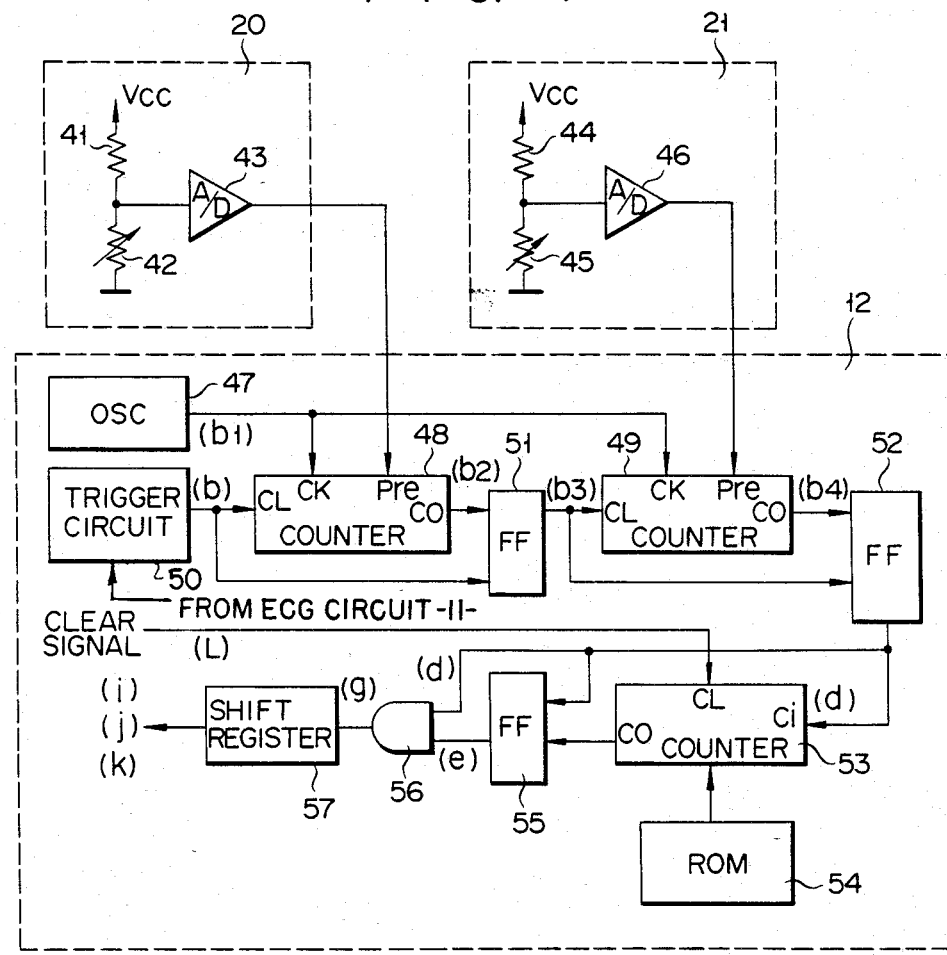
FIG. 4 is a circuit diagram of an electrocardiographic gate used in the blood flow sensing apparatus of FIG. 1.

Turning now to FIG. 4, there is shown a detailed circuit arrangement of the ECG gate 12 and the preset circuits 20 and 21.

The switch circuit 20 is made up of a fixed resistor 41 and a variable resistor 42 connected in series between ground and a power source Vcc, and an analog-to-digital (A/D) converter 43 connected to a node between the resistors 41 and 42. The A/D converter 43 converts an analog signal at the node and the resultant digital signal is used for setting a delay time T1 and is applied to a preset terminal Pre of a first counter 48 in the ECG gate 12. The preset circuit 21 is likewise made up of a fixed resistor 44 and a variable resistor 45 connected in series between ground and the power source Vcc, and an A/D converter 46 connected to a node between these resistors 44 and 45. The digital signal produced by the A/D converter 46 is applied as a signal for setting the sampling period T2 to a preset terminal Pre of a second counter 49 in the ECG gate 12.

The construction of the ECG gate circuit 12 will next be given. An oscillator 47 containing a crystal resonator generates a clock pulse signal at a stable frequency, and is connected at the output to clock pulse terminals Ck of the first and second counters 48 and 49. A trigger circuit 50 coupled at the input with the ECG circuit 11 is coupled at the output to a clear terminal CL of the first counter 48 and a first input terminal of a first flip-flop FF 51 of which the second input is connected to the output Co of the first counter 48. The output of the first FF 51 is connected to a clear terminal CL of the second counter 49 and to a first input terminal of a second FF 52 of which the second input terminal is coupled with the output terminal Co of the second counter 49. The output of the second FF 52 is connected to the input terminal Ci of a third counter 55, a first input terminal of a third FF 53 and a first input terminal of an AND gate 56. The Pre terminal of the third counter 53 is connected to a read only memory (ROM) 54 for storing data to direct a number of counts to be counted by the third counter. The output of a clear generator (not shown) externally operated by an operator is connected to the clear (CL) terminal of the third counter 53. The output terminal Co of the third counter 53 is connected to a second input of the third FF 55. The output terminal of the third FF 55 is connected to a second input terminal of the AND gate 56. The output of the AND gate 56 is connected to the input terminal of a shift register 57. The output terminal of the shift register 57 serves as the output terminal of the ECG gate 12.

The operation of the ECG gate circuit shown in FIG. 4 will be described.

Figure 5:
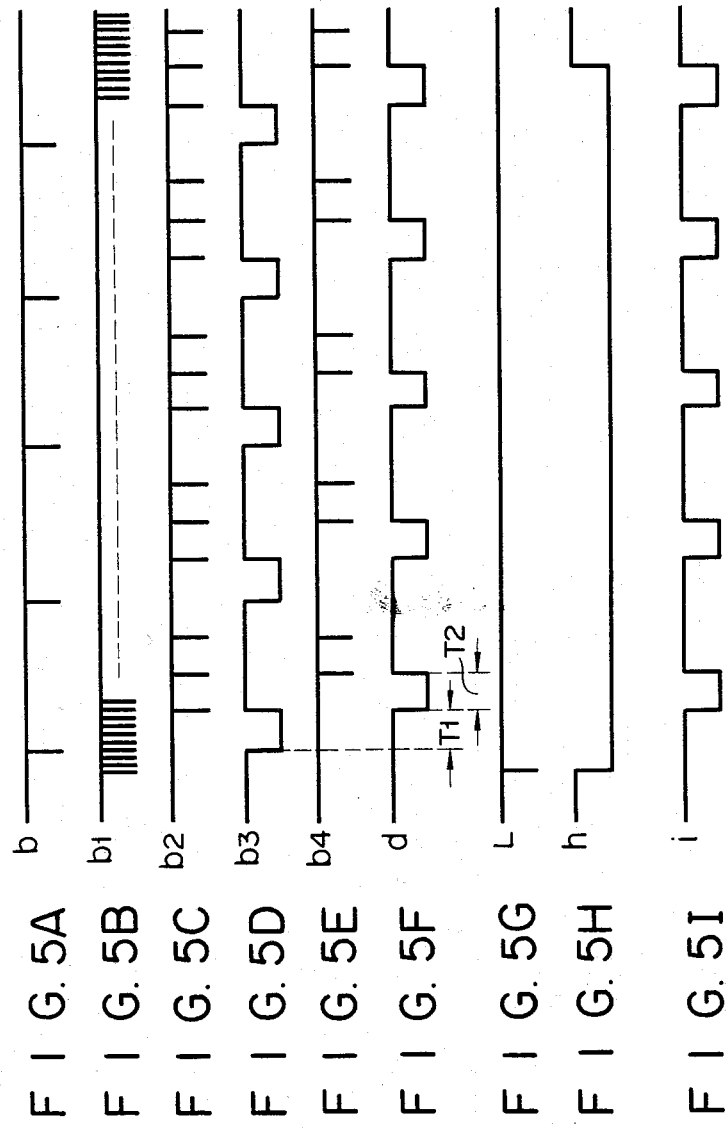
FIGS. 5A to 5I show a set of waveforms at key portions in the electrocardiographic gate of FIG. 4.

The delay time T1 is controlled by a potential at the node between the resistors 41 and 42 in the preset circuit 20. Accordingly, the delay time T1 may be set to a proper value by adjusting the variable resistor 42. A potential at the node properly set by means of the variable resistor 42 is rendered in digital form by the A/D converter 43 and is applied to the Pre terminal of the first counter 48 for presetting the delay time T1. The OSC 47 generates a clock pulse signal at a stable frequency as shown in FIG. 5B. The clock pulse signal is applied to the clock pulse terminal Ck of the first counter 48. Upon receipt of the clock pulse signal, the first counter 48 counts the clock pulse signal from the OSC 47 for the period T1 preset by the preset signal. The trigger circuit 50 produces a trigger pulse signal (FIG. 5A) in synchronism with the peaks of an R wave of the cardiographic signal (FIG. 2A) detected by the ECG circuit 12. The trigger pulse signal is applied as a clear signal to the clear terminal CL of the first counter 48. Upon receipt of the clear pulse signal, the first counter 48 is cleared and then counts incoming clock pulses during the preset delay time, or the period T1. When the first counter completes the count for the period T1, it produces trigger pulses as shown in FIG. 5C. The counter 48 repeats this operation. Those skilled in the art will realize that waveform (c) in FIG. 2C for producing delay period T1 corresponds to waveform (b2) in FIG. 5C with all pulses after the first pulse after each clear signal (which have no effect) removed. The output signal from the counter 48 is coupled with a first input terminal of the FF 51. At this time, the FF 51 receives at the second input terminal the trigger pulses as shown in FIG. 5A. Under this condition, the first FF 51 produces pulse signals as shown in FIG. 5D, which in turn are applied to the clear terminal CL of the second counter 49. The clock pulse signal is applied from the OSC 47 to the clock pulse terminal of the first counter 49. A preset signal for presetting a preset time T2 is applied from the second preset circuit T2 to the Pre terminal of the second counter 49. The second preset circuit operates like the first preset circuit and hence no explanation of its operation will be given. Responsive to the clock pulse signal, the clear signal, and the preset signal, the second counter 49 produces an output signal as shown in FIG. 5E. The output signal from the second counter 49 is applied to the second input terminal of the second FF 52 and the output signal from the first FF 51 is applied to the input terminal of the second counter 49. As a result, an output signal as shown in FIG. 5F is produced from the second FF 52. The output signal from the second FF 52 is applied to the input terminal Ci of the third counter 53, the input terminal of the third FF 55, and the input terminal of the AND gate 56. A signal for providing a preset number of cardiac cycles is applied from the ROM 54 to the preset terminal of the third counter 53. A clear signal is applied from the clear pulse generator to the clear terminal of the third counter 53. The counter 53 receives the output signal from the second FF 52, the preset signal from the ROM 54, and the clear signal from the clear signal generator to produce a pulse signal. The output signal from the third counter 53 is applied to the second input terminal of the third FF 55 and the output signal from the second FF 52 is applied to the input terminal of the third FF 55. As a result, the third FF 54 produces pulses as shown in FIG. 2E. The output signal from the third FF 55 is applied to the second input of the AND gate 56 and the output signal from the second FF 52 is applied to the first input terminal of the AND gate 56. Then, the AND gate 55 produces pulses as shown in FIG. 2G. An output signal from the AND gate 56 is applied to the shift register 57 which then is shifted by one. Accordingly, the shift register 57 produces signals as shown in FIGS. 2I, 2J and 2K.

FIG. 6 shows some examples of displays on the monitor screen. In the figure, a B mode tomogram is displayed on the center part in the screen. Three squared blocks 63 on the upper left corner indicates an average per-minute blood flow given in the digital fashion. Actually, numerals indicating the average per-minute blood flow are displayed at the locations of these three blocks. A cardiographic signal wave is traced on the upper right corner in the screen. The average per-minute blood flow may be easily changed to the average per-cardiac cycle blood flow, if a proper selector is used for this purpose. Further, the digital blood flow may be frozen if a proper freezing means is provided. In the display, the period for averaging the blood flow may be marked to the cardiographic signal wave on the upper right corner, with markers 62 at a different intensity from those of the waveform. In FIG. 7, there are displayed an M mode tomogram 67 on the upper part of the screen, a cardiographic signal wave 68 at the middle part, and Doppler shifts 69 of the blood flow traced on coordinates having the abscissa representing time and the ordinate representing a blood flow velocity at the lower part of the screen. A combination of a blood flow scale marker 70 and a blood flow histogram 71 may be displayed on the same location on the screen as that of the Doppler shift 69, in place of the power spectrums, with provision of a proper selector for selecting either of them. Further, as shown in FIG. 8, an average per-minute blood flow 72 may be substituted for the scale-histogram combination shown in FIG. 7.

As described above, the blood flow sensing apparatus according to the present invention may display an average per-minute or per-cardiac cycle blood flow on the monitor screen, with the combination of the ultrasonic diagnosis device and the Doppler blood flow meter.

Having described a specific embodiment, it should be understood that the invention may be variously changed and modified without departing from the spirit and scope of the invention.

What is claimed is:

1. An ultrasonic Doppler blood flow sensing apparatus:
   transducer means for sequentially transmitting a plurality of ultrasonic beams towards a vessel of a subject and receiving echoes of said beams reflected from said vessel;
   Doppler flow measuring means for analyzing said echoes to obtain an instantaneous velocity of blood in said vessel with every beam, a radius of said vessel and an angle between the said ultrasonic beam and said vessel;
   ECG means for providing an electrocardiographic signal indicating an ECG cycle of said subject; and
   processing means for: (1) integrating said instantaneous velocity over a predetermined portion of a predetermined number of said ECG cycles and providing a blood flow quantity related thereto, (2) averaging said integrated velocity over the most recently occurring said predetermined number of said ECG cycles to produce an average blood flow quantity and (3) updating said integrating and averaging each of said ECG cycles to produce said average blood flow quantity that is constantly current.

2. The blood flow sensing apparatus according to claim 1, wherein said processing means generates said average flow quantity Q2 by $$Q2 = \frac{\sum\limits_{i=1}^{M}(\Sigma vi) \cdot \Delta t}{N} \cdot \frac{\pi r^2}{2} \cdot \cos \theta \ (1/\text{beat})$$

where
   vi: The $i^{th}$ instantaneous average blood flow velocity measurement (cm/s),
   M: Number of detections of Vi,
   N: Number of cardiac cycles during a period of time that M detections of vi occurs,
   $\Delta t$: Time interval for detecting the instantaneous average blood flow signal.

3. The blood flow sensing apparatus according to claim 1 or 2, further comprising means for displaying said average blood flow quantity in an analog fashion.

4. The blood flow sensing apparatus according to claim 1 or 2, further comprising means for displaying said average blood flow quantity in a digital fashion.

5. An ultrasonic Doppler blood flow sensing apparatus as in claim 1 further comprising gating means, responsive to said ECG means, for generating only at predetermined periods with respect to said ECG cycle a sampling signal to cause said instantaneous velocity from said Doppler flow measuring means to be applied to said processing means.

6. An ultrasonic Doppler blood flow sensing apparatus as in claim 5 further comprising means for storing said instantaneous velocity from said Doppler flow measuring means for use by said processing means in response to said sampling signal.

7. The blood flow sensing apparatus according to claim 5 or 6 wherein said gating means further comprises means for controlling the phase and period of said sampling signal in relation to said electrocardiographic signal.

* * * * *